(12) United States Patent
Byrne et al.

(10) Patent No.: US 11,969,369 B2
(45) Date of Patent: *Apr. 30, 2024

(54) STAGED DEPLOYMENT OF EXPANDABLE IMPLANT

(71) Applicant: W. L. Gore & Associates, Inc., Newark, DE (US)

(72) Inventors: Austin A. Byrne, Flagstaff, AZ (US); Patrick M. Norris, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 177 days.

This patent is subject to a terminal disclaimer.

(21) Appl. No.: 17/475,477

(22) Filed: Sep. 15, 2021

(65) Prior Publication Data
US 2022/0000644 A1    Jan. 6, 2022

Related U.S. Application Data

(63) Continuation of application No. 16/767,800, filed as application No. PCT/US2017/051081 on Sep. 12, 2017, now Pat. No. 11,147,698.
(Continued)

(51) Int. Cl.
*A61F 2/954* (2013.01)
*A61F 2/06* (2013.01)
*A61F 2/966* (2013.01)

(52) U.S. Cl.
CPC ........... *A61F 2/954* (2013.01); *A61F 2/06* (2013.01); *A61F 2/9661* (2020.05); *A61F 2002/061* (2013.01); *A61F 2002/9665* (2013.01)

(58) Field of Classification Search
CPC .......... A61F 2/856; A61F 2/954; A61F 2/962; A61F 2/966; A61F 2/9661; A61F 2/9662;
(Continued)

(56) References Cited

U.S. PATENT DOCUMENTS

| 5,873,906 A | 2/1999 | Au et al. |
| 6,030,414 A | 2/2000 | Taheri |

(Continued)

FOREIGN PATENT DOCUMENTS

| CN | 103209660 A | 7/2013 |
| CN | 103945798 A | 7/2014 |

(Continued)

OTHER PUBLICATIONS

International Preliminary Report on Patentability received for PCT Patent Application No. PCT/US2011/060695, dated May 30, 2013, 9 pages.

(Continued)

*Primary Examiner* — Diane D Yabut

(57) ABSTRACT

An endoprosthesis delivery system includes an expandable endoprosthesis including a side branch portal, a first primary sleeve releasably constraining a proximal portion of the expandable endoprosthesis to a collapsed configuration, a second primary sleeve in parallel with the first primary sleeve, the second primary sleeve releasably constraining a distal portion of the expandable endoprosthesis to the collapsed configuration, and a secondary sleeve within the first primary sleeve. Upon release of the first primary sleeve, the secondary sleeve releasably constrains the proximal portion of the expandable endoprosthesis to a partially expanded configuration allowing access to the side branch portal via the partially expanded proximal portion of the expandable endoprosthesis.

21 Claims, 10 Drawing Sheets

Related U.S. Application Data

(60) Provisional application No. 62/394,858, filed on Sep. 15, 2016.

(58) Field of Classification Search
CPC ...... A61F 2/95; A61F 2/97; A61F 2/07; A61F 2002/9623; A61F 2002/9665
See application file for complete search history.

(56) References Cited

U.S. PATENT DOCUMENTS

| | | |
|---|---|---|
| 6,224,627 B1 | 5/2001 | Armstrong et al. |
| 6,315,792 B1 | 11/2001 | Armstrong et al. |
| 6,338,724 B1 | 1/2002 | Dossa |
| 6,352,553 B1 | 3/2002 | Van et al. |
| 6,599,316 B2 | 7/2003 | Vardi et al. |
| 9,226,839 B1 | 1/2016 | Kariniemi et al. |
| 9,592,143 B2 | 3/2017 | Shaw |
| 2001/0007954 A1 | 7/2001 | Shaolian et al. |
| 2002/0029077 A1 | 3/2002 | Leopold et al. |
| 2002/0099431 A1 | 7/2002 | Armstrong et al. |
| 2002/0138129 A1 | 9/2002 | Armstrong et al. |
| 2003/0097169 A1 | 5/2003 | Brucker et al. |
| 2003/0167083 A1 | 9/2003 | Lashinski et al. |
| 2003/0236566 A1 | 12/2003 | Heuser |
| 2004/0093067 A1 | 5/2004 | Israel |
| 2004/0172121 A1 | 9/2004 | Eidenschink et al. |
| 2004/0251668 A1 | 12/2004 | Schneider et al. |
| 2005/0085845 A1 | 4/2005 | Hilaire et al. |
| 2005/0154443 A1 | 7/2005 | Linder et al. |
| 2005/0182476 A1 | 8/2005 | Hartley et al. |
| 2005/0187602 A1 | 8/2005 | Eidenschink |
| 2005/0273151 A1 | 12/2005 | Fulkerson et al. |
| 2006/0004433 A1 | 1/2006 | Greenberg et al. |
| 2006/0015171 A1 | 1/2006 | Armstrong |
| 2007/0083215 A1 | 4/2007 | Hamer et al. |
| 2007/0168020 A1 | 7/2007 | Brucker et al. |
| 2007/0198077 A1 | 8/2007 | Cully et al. |
| 2007/0244547 A1 | 10/2007 | Greenan |
| 2007/0299494 A1 | 12/2007 | Zukowski |
| 2008/0108987 A1 | 5/2008 | Bruszewski et al. |
| 2008/0234717 A1 | 9/2008 | Bruszewski |
| 2008/0269866 A1 | 10/2008 | Hamer et al. |
| 2008/0269867 A1 | 10/2008 | Johnson |
| 2009/0157164 A1 | 6/2009 | Mckinsey et al. |
| 2009/0264821 A1 | 10/2009 | Mafi et al. |
| 2010/0049298 A1 | 2/2010 | Hamer et al. |
| 2010/0063575 A1 | 3/2010 | Shalev et al. |
| 2012/0101563 A1 | 4/2012 | Zhu et al. |
| 2012/0109279 A1 | 5/2012 | Mayberry et al. |
| 2012/0130473 A1 | 5/2012 | Norris et al. |
| 2012/0130475 A1 | 5/2012 | Shaw |
| 2012/0271410 A1 | 10/2012 | Douglas |
| 2013/0211506 A1 | 8/2013 | Dake et al. |
| 2013/0245742 A1 | 9/2013 | Norris |
| 2014/0025162 A1 | 1/2014 | Hamer et al. |
| 2014/0046430 A1 | 2/2014 | Shaw |
| 2014/0135894 A1 | 5/2014 | Norris et al. |
| 2014/0142681 A1 | 5/2014 | Norris |
| 2017/0151079 A1 | 6/2017 | Shaw |
| 2018/0098837 A1 | 4/2018 | Shahriari |
| 2020/0237542 A1 | 7/2020 | Shaw |
| 2020/0368051 A1 | 11/2020 | Byrne et al. |

FOREIGN PATENT DOCUMENTS

| | | |
|---|---|---|
| CN | 104159545 A | 11/2014 |
| CN | 104519838 A | 4/2015 |
| JP | 2002-518086 A | 6/2002 |
| JP | 2003-250907 A | 9/2003 |
| JP | 2004-528066 A | 9/2004 |
| JP | 2007-534367 A | 11/2007 |
| JP | 2010-524629 A | 7/2010 |
| JP | 2010-524630 A | 7/2010 |
| JP | 2014-501563 A | 1/2014 |
| JP | 2015-524341 A | 8/2015 |
| WO | 98/27894 A1 | 7/1998 |
| WO | 1999/065420 A1 | 12/1999 |
| WO | 00/33770 A2 | 6/2000 |
| WO | 00/74595 A1 | 12/2000 |
| WO | 2005/025458 A1 | 3/2005 |
| WO | 2005/070336 A1 | 8/2005 |
| WO | 2005/094726 A1 | 10/2005 |
| WO | 2007/001519 A1 | 1/2007 |
| WO | 2008/133802 A1 | 11/2008 |
| WO | 2010/090699 A1 | 8/2010 |
| WO | 2012/065080 A2 | 5/2012 |
| WO | 2014/025853 A1 | 2/2014 |

OTHER PUBLICATIONS

International Preliminary Report on Patentability received for PCT Patent Application No. PCT/US2017/051081, dated Mar. 28, 2019, 8 pages.

International Search Report and Written Opinion received for PCT Patent Application No. PCT/US2011/060695, dated Oct. 10, 2012, 12 pages.

International Search Report and Written Opinion received for PCT Patent Application No. PCT/US2017/051081, dated Nov. 28, 2017, 10 pages.

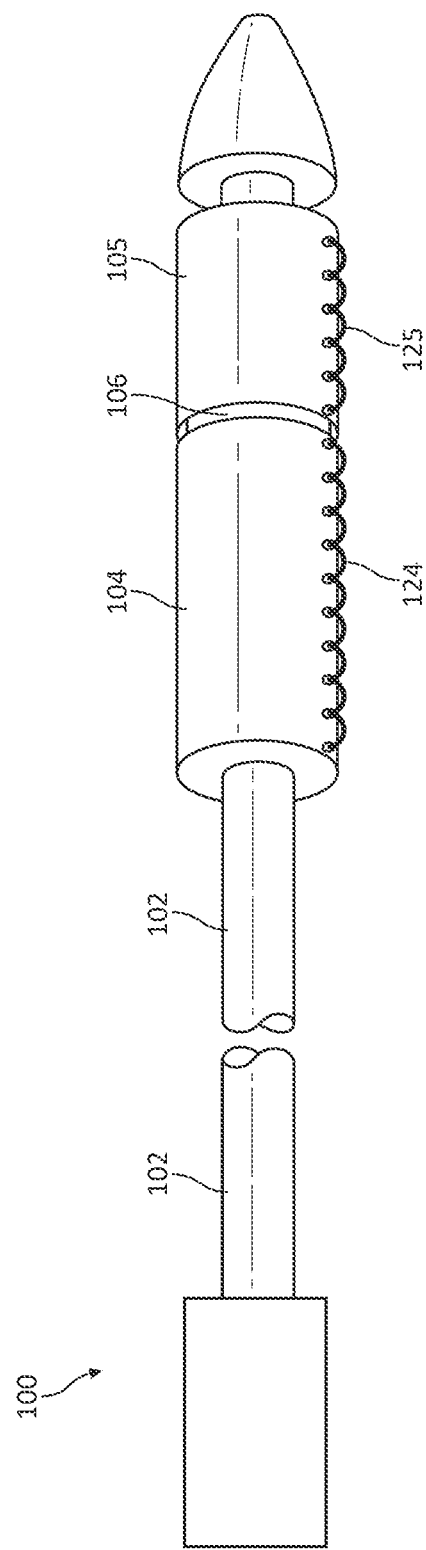

STAGED DEPLOYMENT OF EXPANDABLE IMPLANT

CROSS-REFERENCE TO RELATED APPLICATION

This application is a continuation of U.S. patent application Ser. No. 16/767,800, filed May 8, 2020, which is a national phase application of PCT Application No. PCT/US2017/051081, internationally filed on Sep. 12, 2017, which claims the benefit of U.S. provisional Application No. 62/394,858, filed Sep. 15, 2016, which are herein incorporated by reference in their entireties for all purposes.

TECHNICAL FIELD

The present disclosure relates generally to the delivery and remote deployment of implantable medical devices, including stent grafts.

BACKGROUND

Disease of the vasculature can be difficult for medical practitioners to treat because of the tortuous nature and complexity of the vasculature. By way of example, aortic dissections commonly begin at or near the aortic valve root and continue to the ascending aorta and the aortic arch, and may also affect the upper part of the descending aorta. The three branch vessels off the aortic arch, namely, the brachiocephalic (innominate) artery and the left common carotid and left subclavian arteries, can be anatomically difficult for medical practitioners to access and ultimately treat effectively.

SUMMARY

This disclosure is generally directed to staged deployment techniques for an expandable endoprosthesis including a side branch portal, such as a thoracic branch endoprosthesis. Disclosed staged deployment techniques include endoprosthesis delivery system with first and second primary sleeves in parallel releasably constraining an expandable endoprosthesis to a collapsed configuration, and a secondary sleeve in series with and within the first primary sleeve that releasably constrains the proximal portion of the expandable endoprosthesis to a partially expanded configuration following release of the first primary sleeve. The secondary sleeve can allow access to the side branch portal via a partially expanded proximal portion of the expandable endoprosthesis. The disclosed techniques may be particularly useful for delivery and deployment of an expandable endoprosthesis including a side branch portal within a complex or tortuous vasculature.

In one variation, an endoprosthesis delivery system includes an expandable endoprosthesis including a side branch portal, a first primary sleeve releasably constraining a proximal portion of the expandable endoprosthesis to a collapsed configuration, a second primary sleeve parallel with the first primary sleeve, the second primary sleeve releasably constraining a distal portion of the expandable endoprosthesis to the collapsed configuration, and a secondary sleeve within the first primary sleeve. Upon release of the first primary sleeve, the secondary sleeve releasably constrains the proximal portion of the expandable endoprosthesis to a partially expanded configuration allowing access to the side branch portal via the partially expanded proximal portion of the expandable endoprosthesis.

In another variation, a method of implanting an endoprosthesis within a vasculature of a patient includes inserting a first guidewire into the vasculature, inserting a second guidewire into the a side branch of the vasculature, advancing an expandable endoprosthesis including a side branch portal over the first and second guidewires to a location proximate the side branch, partially expanding a proximal portion of the expandable endoprosthesis while leaving a distal portion of the expandable endoprosthesis fully constrained, advancing a side branch component over the second guidewire into the side branch via the partially expanded proximal portion of the expandable endoprosthesis while the distal portion of the expandable endoprosthesis is fully constrained, locating the expandable endoprosthesis and the side branch component to their intended deployment locations, and fully expanding both the proximal and the distal portions of the expandable endoprosthesis with the side branch component in the side branch.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1 illustrates a side view of a delivery system for an expandable implant, the delivery system including a set of constraining sleeves facilitating staged deployment of the main component;

DETAILED DESCRIPTION

Figure 2A:
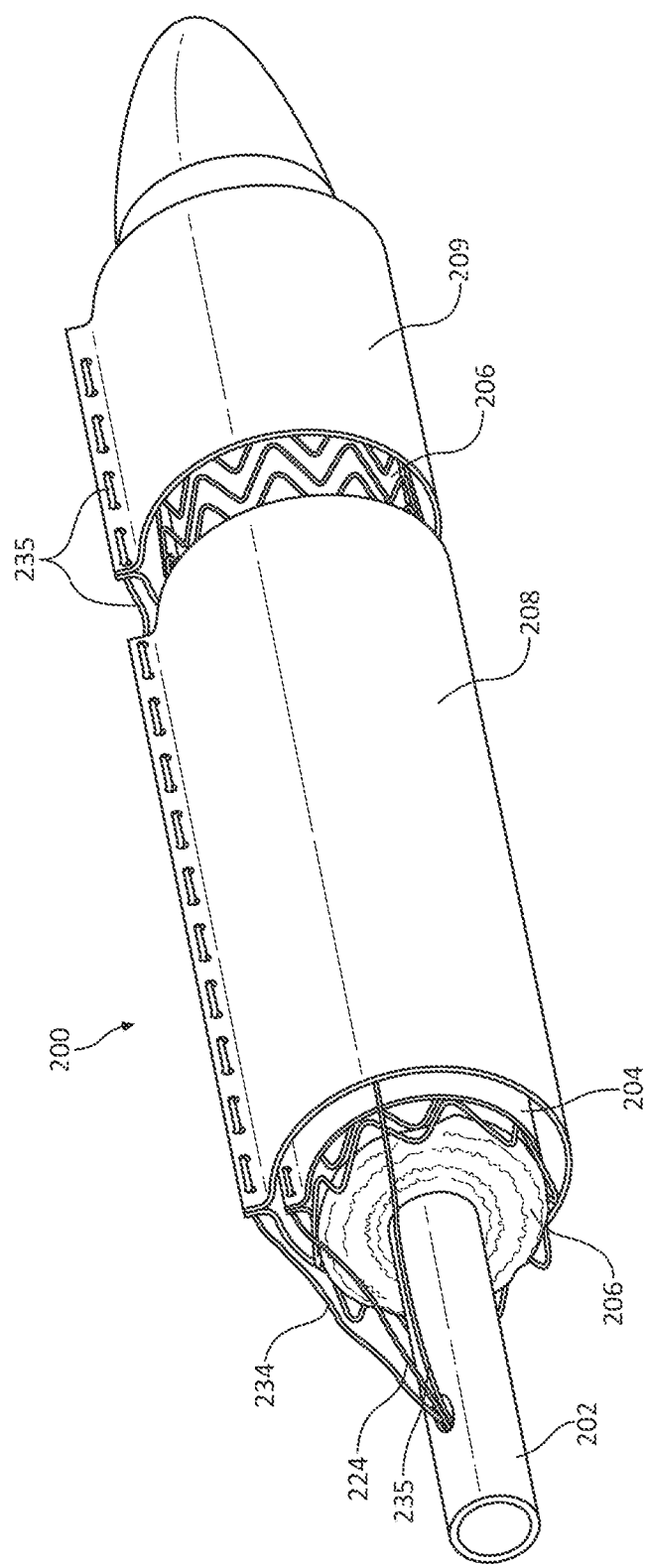
FIGS. 2A and 2B illustrate perspective views of a delivery system for an expandable implant including a main component and a side branch component, the delivery system including a set of constraining sleeves facilitating staged deployment of the main component.

Various examples of the present disclosure are directed to staged deployment techniques for an expandable endoprosthesis including an expandable main component and a side branch portal, such as a thoracic branch endoprosthesis. Disclosed staged deployment techniques include an endoprosthesis delivery system with first and second primary sleeves in parallel releasably constraining an expandable endoprosthesis to a collapsed configuration, and a secondary sleeve within the first primary sleeve that releasably constrains the proximal portion of the expandable endoprosthesis to a partially expanded configuration following release of the first primary sleeve. The secondary sleeve can allow access to the side branch portal via a partially expanded proximal portion of an expandable main component. Allowing positioning of a side branch portal through a partially deployed proximal portion of the main component in an expandable endoprosthesis may allow precise positioning of the expandable main component by allowing the side branch portal to register with a side branch vessel prior to full deployment of the expandable main component.

Example staged deployment techniques for an expandable endoprosthesis including a side branch portal are described with respect to FIGS. 3A-3G. FIGS. 1-2B illustrate perspective views of delivery systems having constraining sleeves such as those described in further detail with respect to FIGS. 3A-3G.

FIG. 1 illustrates a side view of a delivery system 100 for an expandable implant including a main component and a side branch component, delivery system 100 including a set of constraining sleeves 104, 105 facilitating staged deployment of the main component; in this example, the main component is expandable implant 106. Expandable implant 106 can comprise any endoluminal device suitable for delivery to the treatment area of a vasculature. Such devices may include, for example, stents, grafts, and stent grafts. Thus, expandable implant 106 can include one or more stent components with one or more associated graft members disposed over and/or under the stent, which can dilate from a delivery diameter, through a range of larger intermediary diameters, and toward a maximal, pre-determined functional diameter.

For example, expandable implant 106 may include one or more stent components made of nitinol and a graft member made of ePTFE, such as an ePTFE film. However, and as discussed below, any suitable combination of stent component(s) and graft member(s) is within the scope of the present disclosure.

Stent components of expandable implant 106 can have various configurations such as, for example, rings, cut tubes, wound wires (or ribbons) or flat patterned sheets rolled into a tubular form. Stent components can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stent components can also comprise bioresorbable materials such as poly(amino acids), poly(anhydrides), poly(caprolactones), poly(lactic/glycolic acid) polymers, poly(hydroxybutyrates) and poly(orthoesters). Any expandable stent component configuration which can be delivered by a catheter is in accordance with the present disclosure.

Potential materials for graft members of expandable implant 106 include, for example, expanded polytetrafluoroethylene (ePTFE), polyester, polyurethane, fluoropolymers, such as perfluoroelastomers and the like, polytetrafluoroethylene, silicones, urethanes, ultra-high molecular weight polyethylene, aramid fibers, and combinations thereof. Other examples for a graft member material can include high strength polymer fibers such as ultra-high molecular weight polyethylene fibers (e.g., Spectra®, Dyneema Purity®, etc.) or aramid fibers (e.g., Technora®, etc.). The graft member may include a bioactive agent. In one example, an ePTFE graft includes a carbon component along a blood contacting surface thereof. Any graft member that can be delivered by a catheter is contemplated for use in accordance with the present disclosure.

In various examples, a stent component and/or graft member of expandable implant 106 can comprise a therapeutic coating. In these examples, the interior and/or exterior of the stent component and/or graft member can be coated with, for example, a CD34 antigen. Additionally, any number of drugs or therapeutic agents can be used to coat the graft member, including, for example heparin, sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, and thalidomide, among others.

In various examples, expandable implant 106 can comprise a radially collapsed configuration suitable for delivery to the treatment area of the vasculature of a patient. Expandable implant 106 can be constrained toward a radially collapsed configuration and releasably mounted onto a delivery device such as catheter shaft 102. The diameter of expandable implant 106 in the collapsed configuration is small enough for expandable implant 106 to be delivered through the vasculature to the treatment area. In various examples, the diameter of the collapsed configuration is small enough to minimize the crossing profile of delivery system 100 and reduce or prevent tissue damage to the patient. In the collapsed configuration, expandable implant 106 can be guided by catheter shaft 102 through the vasculature.

In various examples, expandable implant 106 can comprise a radially expanded configuration suitable for implanting the device in the treatment area of a patient's vasculature. In the expanded configuration, the diameter of expandable implant 106 can be approximately the same as the vessel to be repaired. In other examples, the diameter of expandable implant 106 in the expanded configuration can be larger than the vessel to be treated to provide a traction fit within the vessel.

In various examples, expandable implant 106 can comprise a self-expandable device, such as a self-expandable stent graft. Self-expandable devices dilate from a radially collapsed configuration to a radially expanded configuration when unconstrained. In other examples, expandable implant 106 can comprise a device that is expanded with the assistance of a secondary device such as, for example, a balloon. In any of these examples, expandable implant 106 may represent an expandable main component of an expandable endoprosthesis including an expandable main component and a side branch, such as expandable main component 206, as described with respect to FIGS. 2A and 2B. In this manner, the descriptions of expandable implant 106 also apply to expandable main component 206, and the description of expandable main component 206 may also apply to expandable implant 106.

Within delivery system 100, sleeves 104, 105 each include a single coupling member woven through openings in edges of a sheet to form the tubular configurations of sleeves 104, 105 from single sheets of material. Specifically, coupling member 124 is woven through openings in the sheet of sleeve 104, and coupling member 125 is woven through openings in the sheet of sleeve 105. In this manner, coupling member 124 secures the edges of sleeve 104 such that sleeve 104 maintains a proximal portion of expandable implant 106 toward a reduced diameter or outer peripheral dimension suitable for endoluminal delivery. Likewise, coupling member 125 secures the edges of sleeve 105 such that sleeve 105 maintains a distal portion of expandable implant 106 toward a reduced diameter or outer peripheral dimension suitable for endoluminal delivery.

Release of sleeves 104, 105 allows expandable implant 106 to expand to a deployed or partially deployed configuration. Specifically, disengaging coupling member 124 from sleeve 104 releases sleeve 104 to allow a proximal portion of expandable implant 106 expanded toward a larger diameter or outer peripheral dimension. Likewise, disengaging coupling member 125 from sleeve 105 releases sleeve 105 to allow a distal portion of expandable implant 106 expanded toward a larger diameter or outer peripheral dimension. Thus, the proximal and distal portions of expandable implant 106 can be separately released in a staged deployment as facilitated by the parallel configuration of sleeves 104, 105.

After release, sleeves 104, 105 can be removed in order to allow expandable implant 106 to expand toward a functional diameter and achieve a desired therapeutic outcome. Alternatively, sleeves 104, 105 can remain coupled to expandable implant 106 or otherwise implanted while not interfering with expandable implant 106.

For either self-expandable or balloon-expandable configurations, sleeves 104, 105 constrain expandable implant 106 in a collapsed configuration for endoluminal delivery of expandable implant 106 to a treatment portion of the vasculature of a patient. For the purposes of the disclosure, the term "constrain" may mean (i) to limit the expansion, either through self-expansion or assisted by a device, of the diameter of an expandable implant or (ii) to cover or surround but not otherwise constrain an expandable implant (e.g., for storage or biocompatibility reasons and/or to provide protection to the expandable implant and/or the vasculature). In delivery system 100, for example, sleeves 104, 105 surround and constrain expandable implant 106 toward a reduced diameter or collapsed configuration.

To facilitate staged deployment as discussed herein, medical systems comprise multiple sleeves including parallel sleeves (at least partially not overlapping) and in series (includes a secondary sleeve overlapped by one or more primary sleeves). Parallel sleeves each constrain different portions of an expandable implant at the same time, whereas sleeves in series are each configured to constrain overlapping portions of an expandable implant. Generally, sleeves in series will constrain the overlapping portions of an expandable implant at different sizes with the outer sleeve of sleeves in series being configured to constrain the overlapping portions of the expandable implant to a smaller size than the configuration of inner sleeve(s) of the sleeves in series. In this manner, the inner sleeve(s) of the sleeves in series may only constrain the overlapping portions of the expandable implant after the release of any outer sleeves constraining the overlapping portions of the expandable implant.

When expandable implant 106 is in a desired position within the vasculature, coupling members 124, 125 can each be disengaged from sleeves 104, 105, respectively, from outside of the body of the patient, which allows sleeves 104, 105 to open and expandable implant 106 to expand. In various examples, expandable implant 106 can be self-expanding, or expandable implant 106 can be expanded by an expanding device, such as a balloon.

In some examples, coupling members 124, 125 can be disengaged by applying sufficient tension to their respective proximal portions. For example, one or more translatable elements can be attached to coupling members 124, 125 outside of the body. Displacement of the translatable elements, such as rotation of a dial or rotational member or translation of a handle or knob, may provide sufficient tension to displace and disengage coupling members 124, 125. In another example, coupling members 124, 125 can be disengaged from sleeves 104, 105 by a mechanical mechanism (not shown), such as a cutting edge or other mechanism operated from outside of the body of the patient.

In various examples, the parallel configuration of sleeves 104, 105 facilitates staged deployment of expandable implant 106 by allowing separate expansion of proximal and distal portions of expandable implant 106. As described with respect to FIGS. 2A and 2B and delivery system 200, such control may facilitate delivery of a side branch component into a side branch vessel through an expanded proximal portion of expandable implant 106.

Figure 2B:
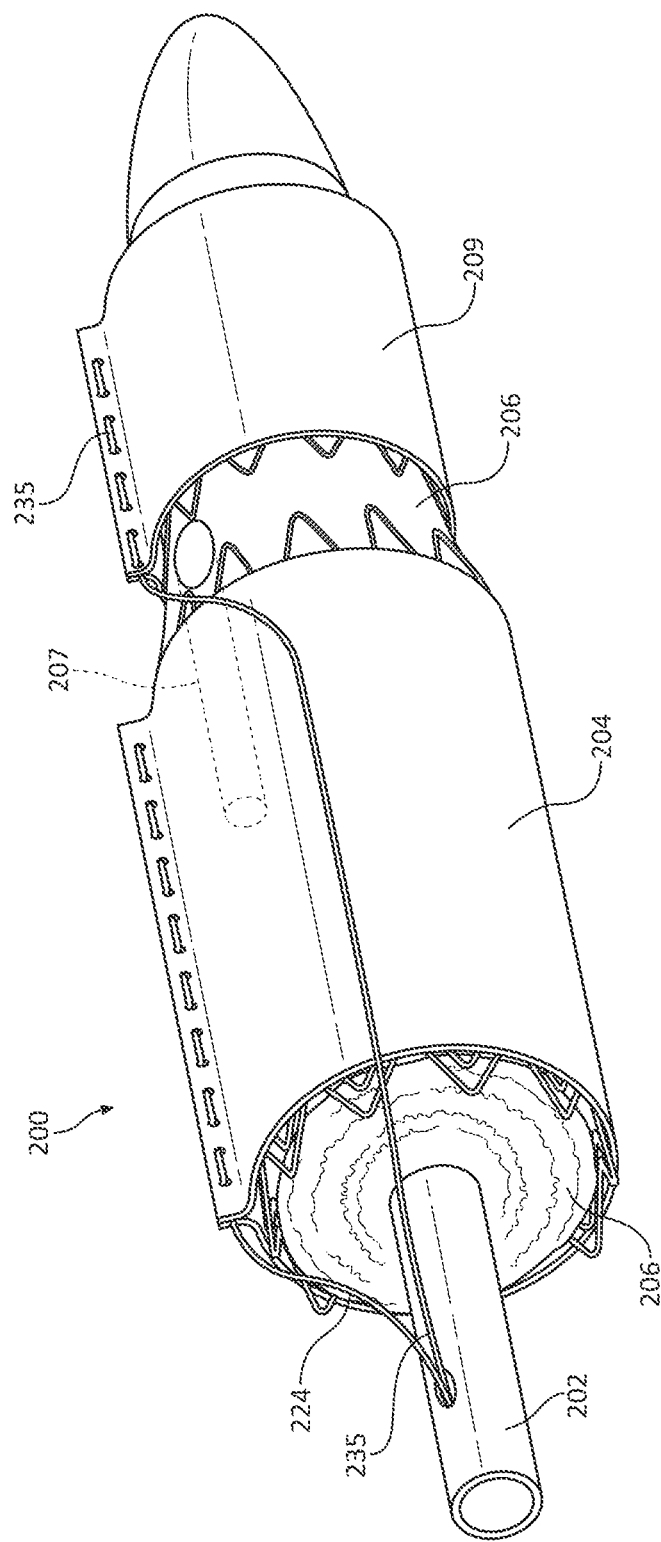
Figure 3A:
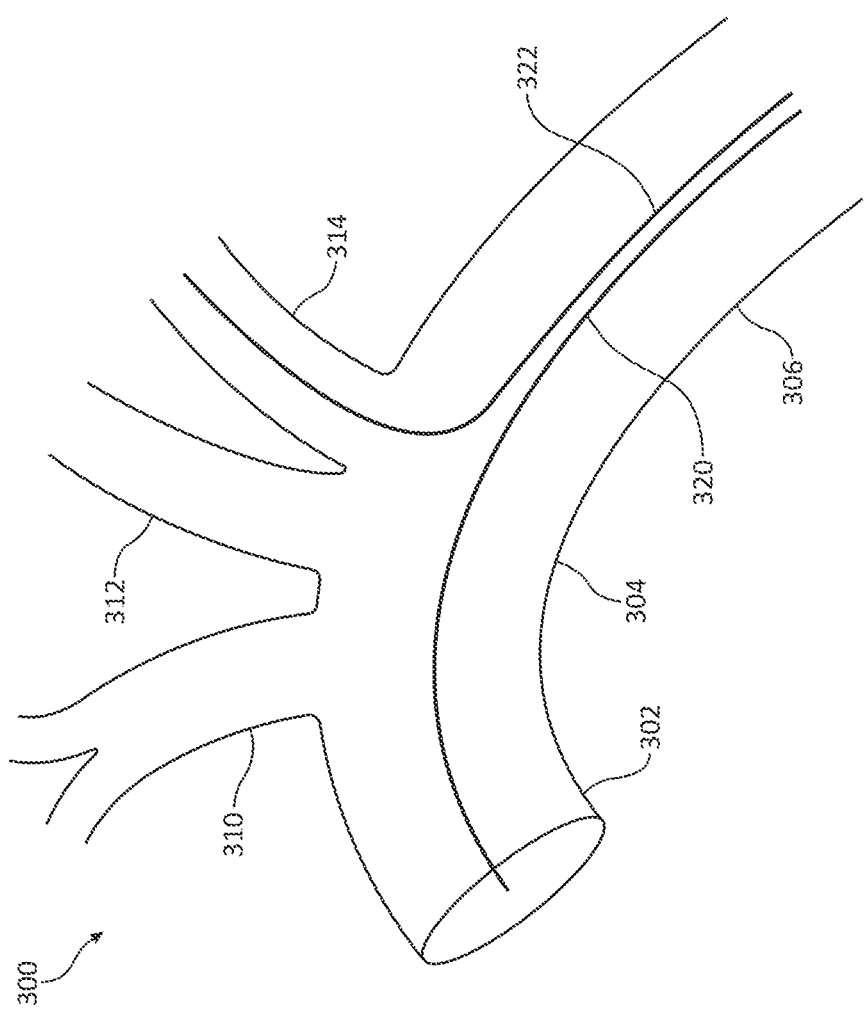
FIGS. 3A-3G illustrate staged deployment of an expandable implant including a main component and a side branch component using the delivery system of FIGS. 2A and 2B in the thoracic aorta of a patient.
Figure 3B:
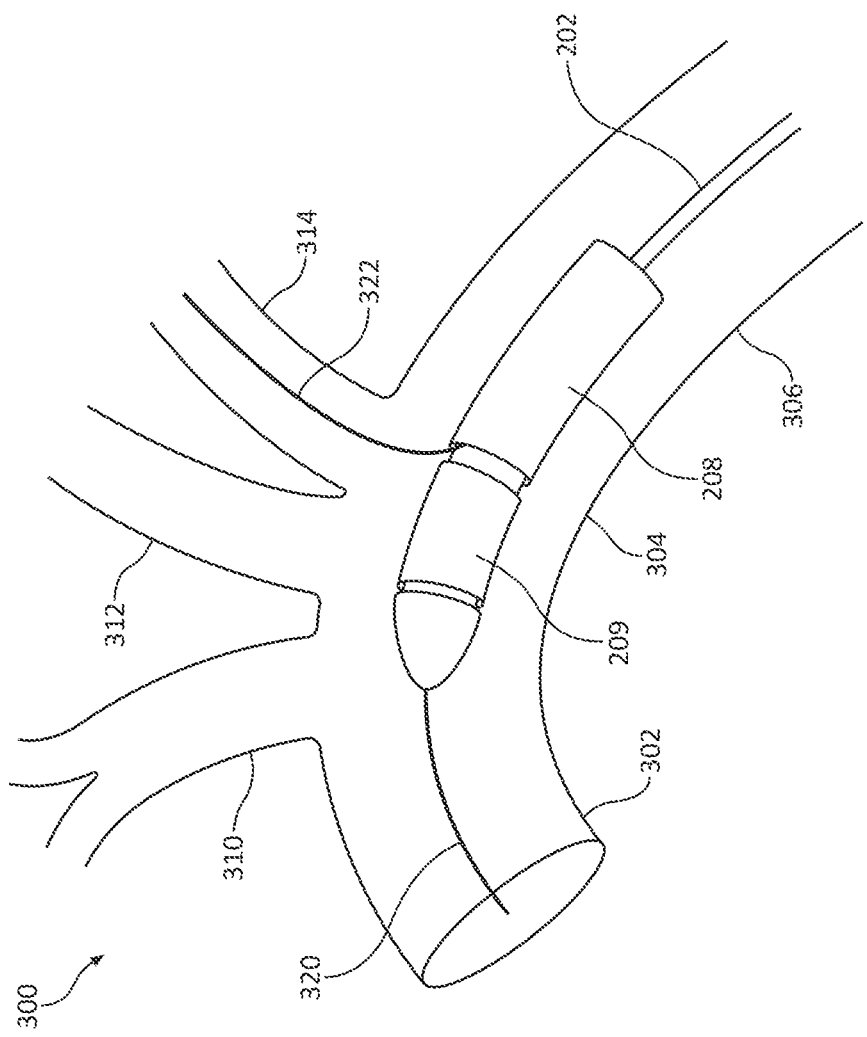
Figure 3C:
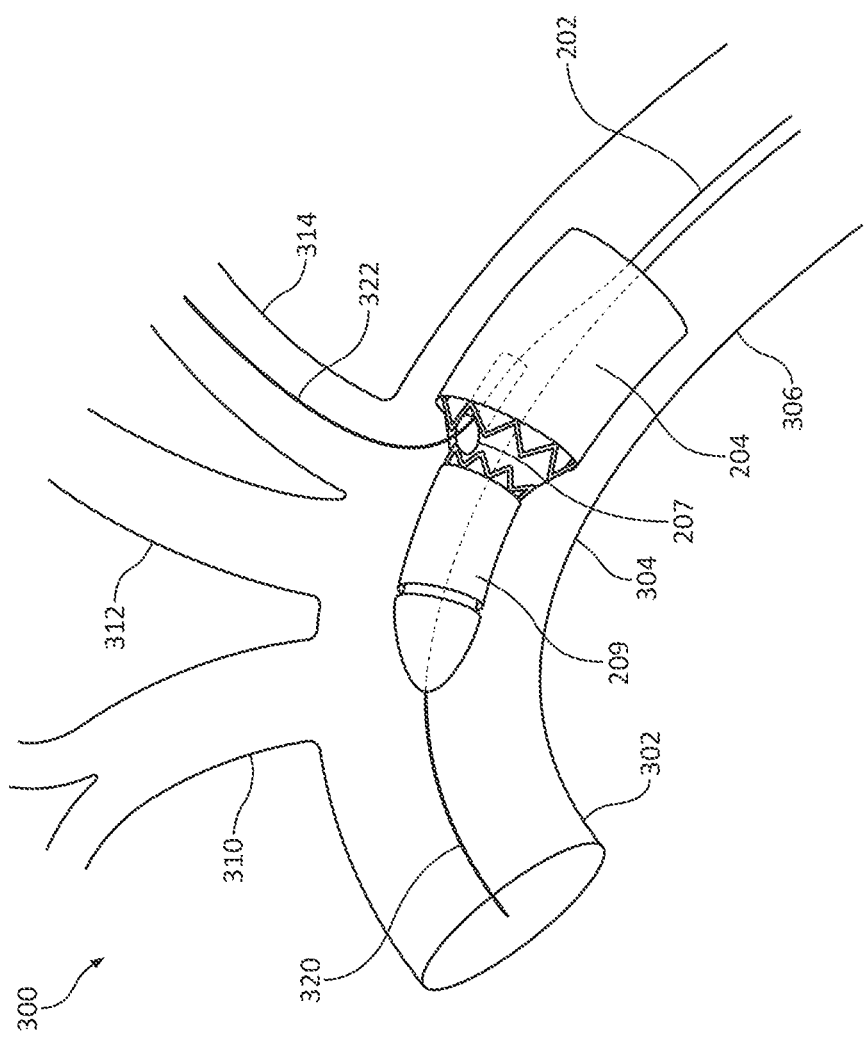
Figure 3D:
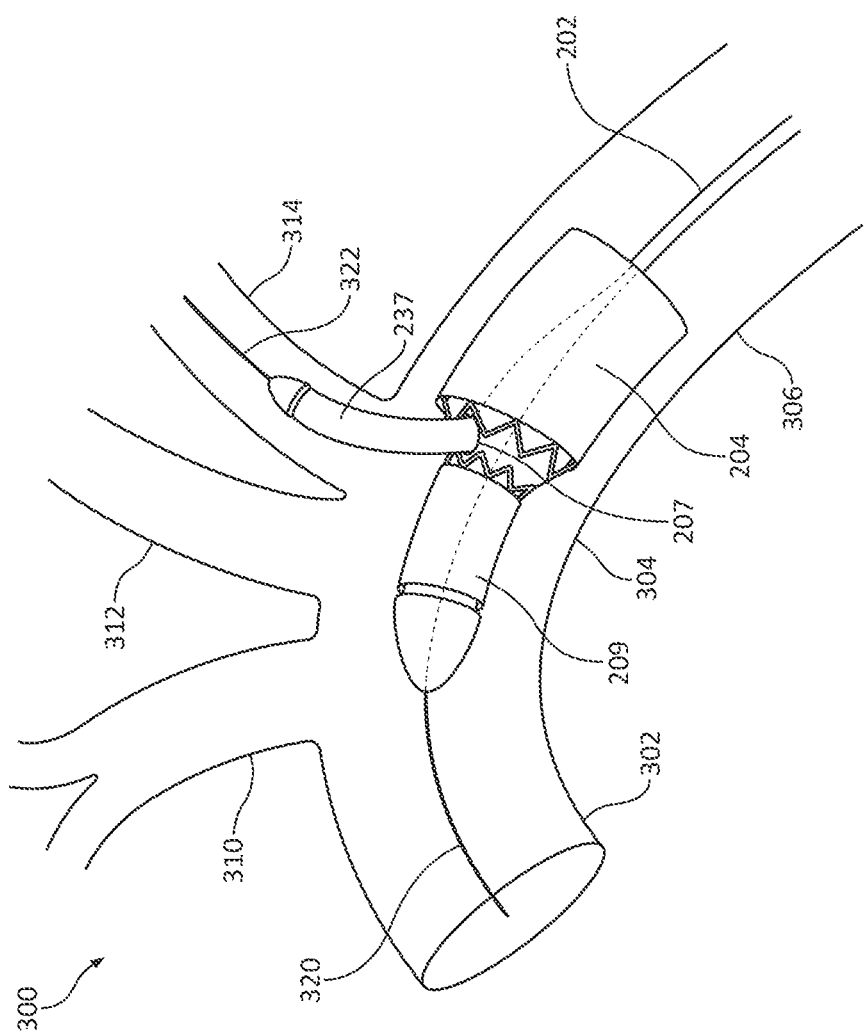
Figure 3E:
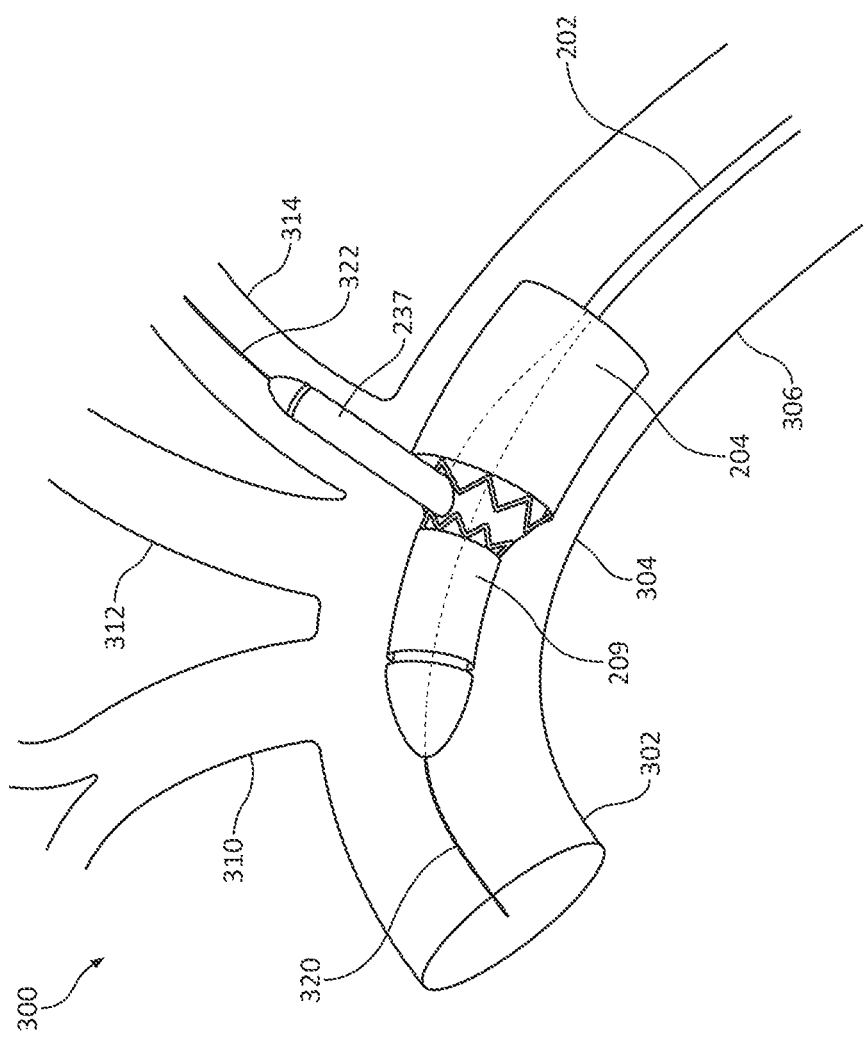
Figure 3F:
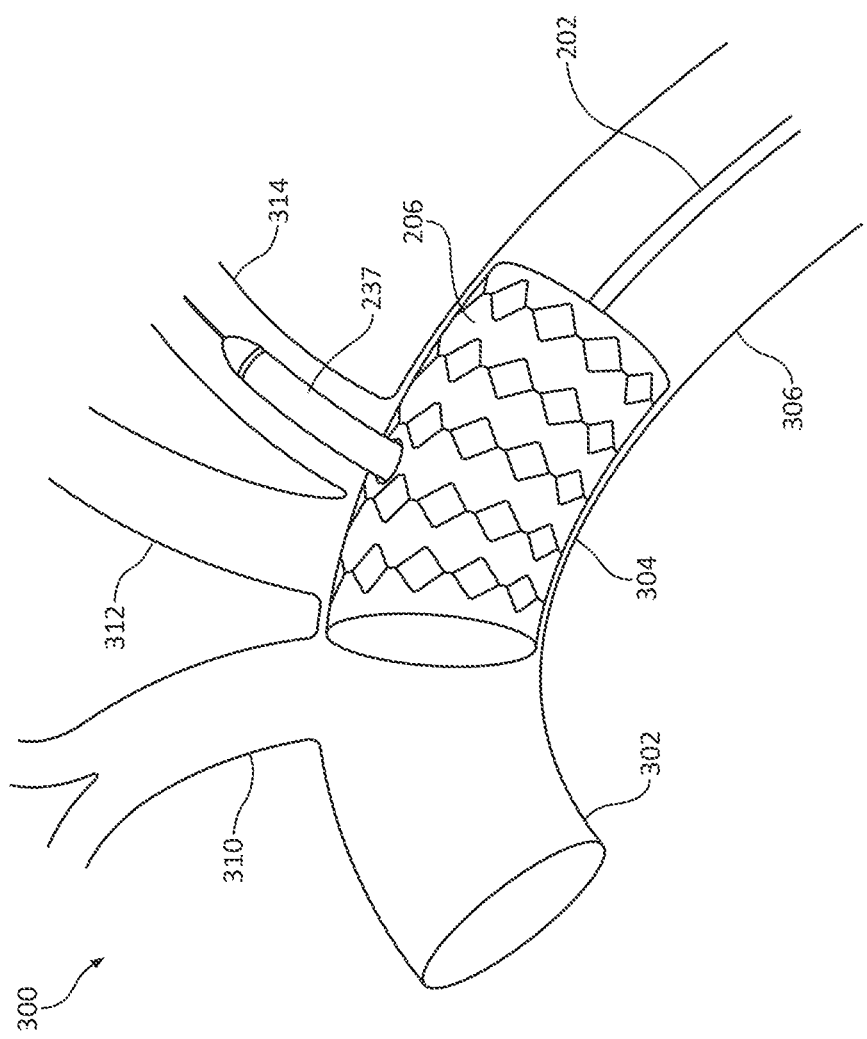
Figure 3G:
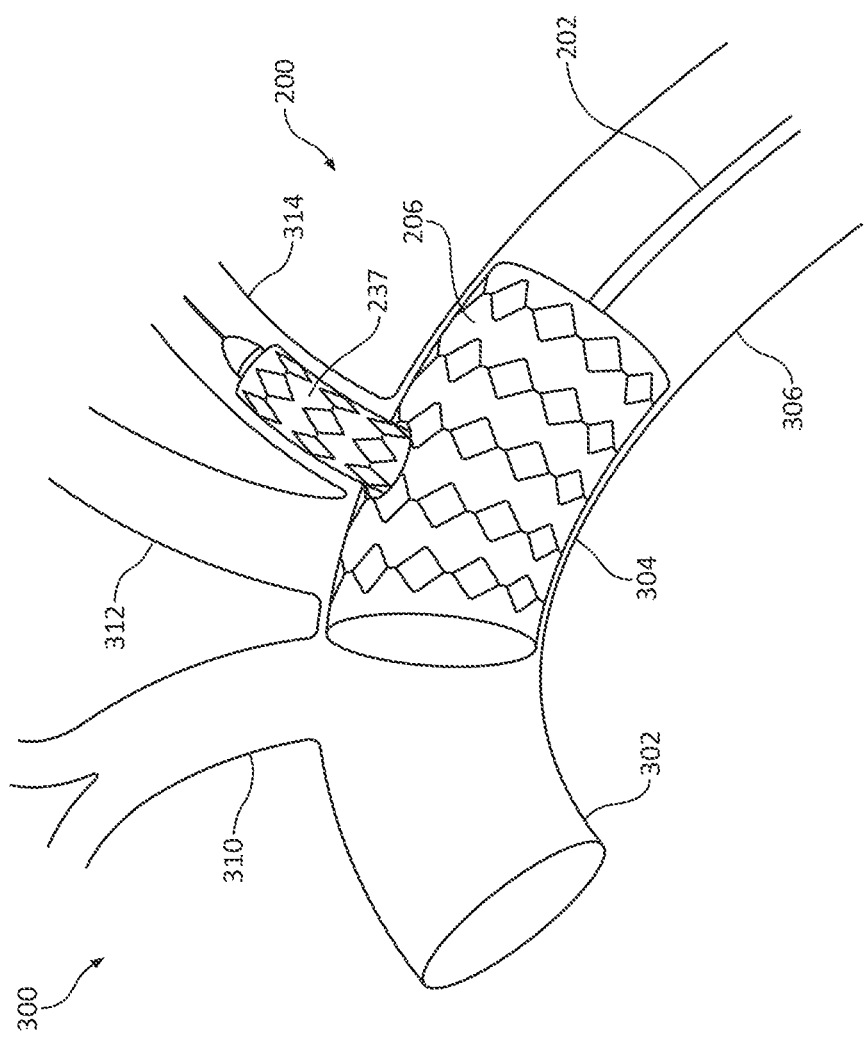

FIGS. 2A and 2B illustrate perspective views of a delivery system 200 for an expandable implant 201 (FIG. 3G). Expandable implant 201 includes an expandable main component 206 and a side branch component 237. Delivery system 200 includes expandable main component 206 releasably mounted onto catheter shaft 202. Delivery system 200 also includes a set of constraining sleeves 204, 208, 209 facilitating staged deployment of expandable main component 206.

While expandable main component 206 combines with side branch component 237 to form expandable implant 201, expandable main component 206 itself also represents an expandable implant in that expandable main component 206 may be independently deployed in a vasculature without any other components. In this manner, expandable main component 206 represents one example of expandable implant 106 as described with respect to FIG. 1. In the same or different examples, expandable main component 206 represents an expandable endoprosthesis, such as a stent, a graft, or a stent graft. For example, expandable main component 206 may include one or more stent components made of nitinol and a graft member made of ePTFE. However, any suitable combination of stent component(s) and graft member(s) is within the scope of the present disclosure, including, but not limited to the description of stent component(s) and graft member(s) discussed with respect to expandable implant 106.

As shown in FIG. 2A, expandable main component 206 is constrained by a set of sleeves which circumferentially surrounds expandable main component 206. Specifically, delivery system 200 comprises primary sleeves 208, 209 and secondary sleeve 204. Primary sleeves 208, 209 circumferentially surround expandable main component 206 and constrain it toward a collapsed configuration, in which the diameter is less than the diameter of an unconstrained or otherwise deployed implant for delivery within the vasculature. Primary sleeves 208, 209 are in parallel with one another. Specifically, primary sleeve 208 releasably constrains a proximal portion of expandable main component 206, and primary sleeve 209 releasably constrains a distal portion of expandable main component 206. Secondary sleeve 204 is in series with and within primary sleeve 208. As shown in FIG. 2B, upon release of primary sleeve 208, secondary sleeve 204 releasably constrains the proximal portion of expandable main component 206 to a partially expanded configuration allowing access to side branch portal 207 via the partially expanded proximal portion of expandable main component 206.

In a collapsed configuration within sleeves 204, 208, 209, expandable main component 206 can be introduced to a vasculature and directed by a delivery system to a treatment area of the vasculature. Once in position in the treatment area of the vasculature, sleeves 204, 208, 209 may be released according to the staged deployment techniques described with respect to FIGS. 3A-3G, and expandable main component 206 can be expanded to an expanded configuration.

For example, as shown in FIG. 2A, coupling member 234 secures the edges of sleeve 208 such that sleeve 208 maintains a proximal portion of expandable main component 206 toward a reduced diameter or outer peripheral dimension suitable for endoluminal delivery. Likewise, coupling member 235 secures the edges of sleeve 209 such that sleeve 209 maintains a distal portion of main component 206 toward a reduced diameter or outer peripheral dimension suitable for endoluminal delivery.

In various examples, sleeves 204, 208, 209 are formed from a sheet of one or more materials wrapped or folded about expandable main component 206. For each sleeve, the sheet of material(s) used to form the sleeve comprises a series of openings, such that the openings extend from one edge of the sheet to the other. Coupling members 224, 234, 235 are woven or stitched through the series of openings in the sheets of material(s), securing each of the two edges together and forming a tube. In various examples, coupling members 224, 234, 235 can comprise a woven fiber. In other examples, coupling members 224, 234, 235 can comprise a monofilament fiber. Any type of string, cord, thread, fiber, or wire which is capable of maintaining a sleeve in a tubular shape is within the scope of the present disclosure. While the illustrative examples herein are described as comprising one or more tubular sleeves, sleeves of any non-tubular shape that corresponds to an underlying expandable implant or that are otherwise appropriately shaped for a given application are also within the scope of the present disclosure.

As shown in FIG. 2B, following the release of sleeve 208 and coupling member 235, coupling member 224 secures the edges of secondary sleeve 204 such that secondary sleeve 204 maintains the proximal portion of expandable main component 206 toward an intermediate configuration larger than the collapsed configuration and smaller than the deployed configuration suitable for precise positioning of expandable main component 206 adjacent a target location within a vasculature. In the intermediate configuration, the proximal portion of expandable main component 206 is constrained in a diameter smaller than the expanded configuration and larger than the collapsed configuration. For example, the diameter of proximal portion of expandable main component 206 in the intermediate configuration can be about 70% of the diameter of the proximal portion of expandable main component 206 in the expanded configuration. However, any diameter of the intermediate configuration which is less than the diameter of the expanded configuration and larger than the collapsed configuration is contemplated by this disclosure.

With reference to FIG. 2B, after primary sleeve 208 has been expanded, secondary sleeve 204 constrains the expandable main component 206 toward the intermediate configuration. In the intermediate configuration, expandable main component 206 can be oriented and adjusted (e.g., by bending and torsional rotation) to a desired location within the treatment area of the vasculature. In specific embodiments, such precise positioning may include delivering a side branch component through side branch portal 207, which is exposed following the partial expansion of the proximal portion of expandable main component 206 toward an intermediate configuration.

In various examples, expandable main component 206 may comprise a fenestratable portion covering side branch portal 207. In such configurations, expandable main component 206 may include a frangible material which may be fenestrated by an endoluminal tool after expandable main component 206 has been partially or completely implanted in the vasculature of a patient. Once fenestrated, fenestratable portion may be used, for example, to install branching stent grafts to expandable main component 206. Side branch fenestrations allow for branching devices, such as branching stent grafts, to be connected to and in with communication expandable main component 206. Such fenestrations and branching stent grafts may facilitate conforming expandable main component 206 and additional branching stent grafts to the anatomy of a patient, such as iliac arteries and associated vascular branches.

FIGS. 3A-3G illustrate techniques for implanting, including positioning and deployment, expandable implant 201 using the delivery system of FIGS. 2A and 2B in thoracic aorta 300 of a patient. The techniques of FIGS. 3A-3G may be used to treat a thoracic aortic aneurysm of thoracic aorta 300 of a patient. However, the disclosed examples are not limited to implantation within thoracic aorta 300 and may be readily applied to other vasculatures including one or more side branches. In the particular example, of FIGS. 3A-3G, thoracic aorta 300 includes ascending aorta 302, aortic arch 304 and descending aorta 306. Side branch vessels, including brachiocephalic trunk artery 310, left common carotid artery 312, and left subclavian artery 314 extend from thoracic aorta 300.

As shown in FIG. 3A, guidewires 320, 322 are inserted into the vasculature. Specifically, guidewire 320 is inserted into thoracic aorta 300, whereas guidewire 322 is inserted into a side branch via thoracic aorta 300. In the example of FIG. 3A, guidewire 322 is inserted into left subclavian artery 314 via thoracic aorta 300 although in other examples, guidewire 322 may be inserted into a different side branch, such as brachiocephalic trunk artery 310 or left common carotid artery 312.

As shown in FIG. 3B, main component 206 is advanced over guidewires 320, 322 to a location proximate the side branch of the vasculature, in this example, left subclavian artery 314. Whereas guidewire 320 is routed through a central lumen a main component 206 before exiting a distal end of main component 206, guidewire 322 is routed through the central lumen of main component 206, before passing through side branch portal 207. Due to the routing of guidewire 322 through the central lumen of main component 206, advancement of main component 206 meets resistance once the opening of side branch portal 207 is adjacent the side branch, left subclavian artery 314.

As shown in FIG. 3C, following the advancement of main component 206, an expandable endoprosthesis including a side branch portal 207, over guidewires 320, 322 to a location proximate the side branch, left subclavian artery 314, a proximal portion of main component 206 is partially expanded. For example, coupling member 234 may be activated to release primary sleeve 208 to allow a proximal portion of main component 206 to expand to an intermediate configuration filling secondary sleeve 204. In the intermediate configuration, the proximal portion of expandable main component 206 is constrained in a diameter smaller than the expanded configuration and larger than the collapsed configuration. During the partial expansion of the proximal portion of main component 206, the distal portion of main component 206 remains fully constrained by primary sleeve 209. Following partial expansion of the proximal portion of main component 206, side branch portal 207 exits expandable main component 206 via a space between primary sleeve 209 and secondary sleeve 204.

As shown in FIG. 3D, following the partial expansion of the proximal portion of expandable main component 206, side branch component 237 is advanced over guidewire 322, through catheter shaft 202, into a proximal portion of the central lumen of expandable main component 206, exiting the central lumen of expandable main component 206 via side branch portal 207. During this advancement of side branch component 237, the proximal portion of main component 206 remains in an intermediate configuration constrained by primary sleeve 204, and the distal portion of main component 206 remains fully constrained by primary sleeve 209.

As shown in FIG. 3E, expandable main component 206 and side branch component 237 are located to their intended deployment locations. For example, expandable main component 206 and side branch component 237 may be located to their intended deployment locations by locating expandable main component 206 within thoracic aorta 300 such that the side branch component 237 registers with the side branch, left subclavian artery 314.

As shown in FIG. 3F, after, expandable main component 206 and side branch component 237 are located to their intended deployment locations, expandable main component 206 is fully expanded by release of distal primary sleeve 209 and proximal secondary sleeve 204. For example, coupling member 235 may be activated to release primary sleeve 209 to allow the distal portion of main component 206 to fully expand from the fully collapsed configuration, and coupling member 224 may be activated to release secondary sleeve 204 to allow the proximal portion of main component 206 to fully expand from the intermediate configuration. As side branch component 237 is already located within the side branch, left subclavian artery 314, full expansion of main component 206 occurs with side branch portal 207 in proper alignment with left subclavian artery 314. Guidewire 320 may optionally be withdrawn after the full expansion of expandable main component 206.

As shown in FIG. 3G, after, expandable main component 206 is fully expanded, side branch component 237 is fully expanded within the side branch, left subclavian artery 314, to form expandable implant 201 including main component 206 and side branch component 237. For example, side branch component 237 may be self-expanding or balloon expanding. In either example, side branch component 237 may include a removable sleeve that may be removed to facilitate expansion within left subclavian artery 314. In other examples, a sleeve may be retained on side branch component 237 following expansion or side branch component 237 may be constrained and released by other techniques, such as a suture. Guidewire 322 may optionally be withdrawn after the full expansion of side branch component 237. Catheter 202 may also be withdrawn.

Optionally, additional side branch components (not shown) may also be deployed within other side branches, such as brachiocephalic trunk artery 310 or left common carotid artery 312. For example, main component 206 may comprise fenestratable portion(s) generally aligned with other side branches following the expansion of main component 206. Such side branch components may be implanted to be connected to and in communication with expandable main component 206 via catheter 202 or otherwise according to any suitable techniques. Such fenestrations and additional branching stent grafts may facilitate conforming expandable main component 206, side branch component 237 and additional branching stent grafts to the anatomy of a patient, including brachiocephalic trunk artery 310, left common carotid artery 312, and left subclavian artery 314.

Some representative examples of this disclosure may be characterized according to the following clauses.

Clause 1: An endoprosthesis delivery system comprising: an expandable endoprosthesis including a side branch portal, a first primary sleeve releasably constraining a proximal portion of the expandable endoprosthesis to a collapsed configuration, a second primary sleeve in parallel with the first primary sleeve, the second primary sleeve releasably constraining a distal portion of the expandable endoprosthesis to the collapsed configuration, and a secondary sleeve within the first primary sleeve. Upon release of the first primary sleeve, the secondary sleeve releasably constrains the proximal portion of the expandable endoprosthesis to a partially expanded configuration allowing access to the side branch portal via the partially expanded proximal portion of the expandable endoprosthesis.

Clause 2: The endoprosthesis delivery system of clause 1, wherein the side branch portal exits the expandable endoprosthesis via a space between the second primary sleeve and the secondary sleeve.

Clause 3: The endoprosthesis delivery system of clause 1, further comprising a side branch component configured for delivery through the side branch portal via the partially expanded proximal portion of the expandable endoprosthesis.

Clause 4: The endoprosthesis delivery system of clause 1, further comprising: a first guidewire extending through a central lumen of the expandable endoprosthesis, the central lumen extending through both the proximal portion of the expandable endoprosthesis and the distal portion of the expandable endoprosthesis, and a second guidewire extending through the proximal portion of the expandable endoprosthesis and the side branch portal.

Clause 5: The endoprosthesis delivery system of clause 4, further comprising a side branch component configured for delivery over the second guidewire and through the side branch portal via the partially expanded proximal portion of the expandable endoprosthesis.

Clause 6: The endoprosthesis delivery system of clause 1, further comprising a coupling member configured to release the first primary sleeve without releasing either the second primary sleeve or the secondary sleeve.

Clause 7: The endoprosthesis delivery system of clause 6, wherein the coupling member is a first coupling member, the endoprosthesis delivery system further comprising a second coupling member configured to release both the second primary sleeve or the secondary sleeve.

Clause 8: The endoprosthesis delivery system of clause 1, wherein the endoprosthesis includes a balloon expandable stent component.

Clause 9: The endoprosthesis delivery system of clause 1, wherein the endoprosthesis includes a self-expanding stent component.

Clause 10: The endoprosthesis delivery system of clause 1, wherein the endoprosthesis includes a graft component comprising expanded polytetrafluoroethylene (ePTFE) film.

Clause 11: The endoprosthesis delivery system of clause 1, wherein the endoprosthesis is a stent graft.

Clause 12: The endoprosthesis delivery system of clause 1, wherein the expandable endoprosthesis is configured to treat a thoracic aortic aneurysm.

Clause 13: A method of implanting an endoprosthesis within a vasculature of a patient, the method comprising: inserting a first guidewire into the vasculature, inserting a second guidewire into the a side branch of the vasculature, advancing an expandable endoprosthesis including a side branch portal over the first and second guidewires to a location proximate the side branch, partially expanding a proximal portion of the expandable endoprosthesis while leaving a distal portion of the expandable endoprosthesis fully constrained, advancing a side branch component over the second guidewire into the side branch via the partially expanded proximal portion of the expandable endoprosthesis while the distal portion of the expandable endoprosthesis is fully constrained, locating the expandable endoprosthesis and the side branch component to their intended deployment locations, and fully expanding both the proximal and the distal portions of the expandable endoprosthesis with the side branch component in the side branch.

Clause 14: The method of clause 13, further comprising expanding the side branch component within the side branch.

Clause 15: The method of clause 13, wherein locating the expandable endoprosthesis and the side branch component to their intended deployment locations comprises locating the expandable endoprosthesis within the vasculature such that the side branch component registers with the side branch.

Clause 16: The method of clause 13, wherein partially expanding a proximal portion of the expandable endoprosthesis while leaving a distal portion of the expandable endoprosthesis fully constrained comprises releasing a first primary sleeve from the proximal portion of the expandable endoprosthesis while leaving a second primary sleeve over the distal portion of the expandable endoprosthesis, and also leaving a secondary sleeve over the proximal portion.

Clause 17: The method of clause 16, wherein the side branch portal exits the expandable endoprosthesis via a space between the second primary sleeve and the secondary sleeve.

Clause 18: The method of clause 16, wherein fully expanding both the proximal and the distal portions of the expandable endoprosthesis with the side branch component in the side branch comprises releasing the second primary sleeve from the distal portion of the expandable endoprosthesis and releasing the secondary sleeve from the proximal portion of the expandable endoprosthesis.

Clause 19: The method of clause 13, wherein the expandable endoprosthesis is a stent graft.

Clause 20: The method of clause 13, wherein the vasculature includes a thoracic aortic aneurysm.

Various modifications may be made to the disclosed examples within the spirit of this disclosure, especially in matters of structure, materials, elements, components, shape, size and arrangement of parts including combinations within the principles of the disclosure, to the full extent indicated by the broad, general meaning of the terms in which the appended claims are expressed. For example, while a variety of example configurations are provided, numerous additional configurations for endoprosthesis constraining sleeves providing staged deployment can readily be made within the spirit of this disclosure. To the extent that these various modifications and configurations do not depart from the spirit and scope of the appended claims, they are intended to be encompassed therein.

What is claimed is:

1. An endoprosthesis delivery system comprising:
an expandable endoprosthesis including a side branch portal;
a first primary sleeve releasably constraining at least a first portion of the expandable endoprosthesis toward a collapsed configuration;
a secondary sleeve overlapping with the first primary sleeve, wherein upon release of the first primary sleeve, the secondary sleeve releasably constrains a second portion of the expandable endoprosthesis to a partially expanded configuration allowing access to the side branch portal via the partially expanded portion of the expandable endoprosthesis;
a side branch component configured for delivery through the side branch portal via the partially expanded portion of the expandable endoprosthesis.

2. The endoprosthesis delivery system of claim 1, wherein:
the expandable endoprosthesis defines a central lumen, further comprising a first guidewire extended through the central lumen; and
a second guidewire extended through the partially expanded portion of the endoprosthesis and the side branch component.

3. The endoprosthesis delivery system of claim 1, further comprising a second primary sleeve in parallel with the first primary sleeve, the second primary sleeve releasably constraining a third portion of the expandable endoprosthesis to the collapsed configuration.

4. The endoprosthesis delivery system of claim 3, wherein the third portion is a distal portion of the expandable endoprosthesis.

5. The endoprosthesis delivery system of claim 1, wherein the first portion and the second portion are substantially the same.

6. The endoprosthesis delivery system of claim 5, wherein the first portion and the second portion correspond with a proximal portion of the expandable endoprosthesis.

7. A method of deploying an endoprosthesis, the method comprising:
positioning an endoprosthesis within a vasculature;
partially expanding a first portion of the endoprosthesis;
positioning a side branch component via the first portion of the endoprosthesis into a side branch of the vasculature; and
fully expanding the endoprosthesis with the side branch component in the side branch.

8. The method of claim 7, wherein a primary sleeve constrains the endoprosthesis in a delivery configuration and a secondary sleeve constrains the first portion of the endoprosthesis in a partially expanded configuration.

9. The method of claim 8, wherein the first primary sleeve constrains the first portion of the endoprosthesis in the delivery configuration and a second primary sleeve constrains a second portion of the endoprosthesis in a delivery configuration.

10. The method of claim 8, further comprising releasing the primary sleeve without releasing any other sleeve to expand the first portion of the endoprosthesis from the delivery configuration.

11. The method of claim 7, wherein the endoprosthesis is positioned by advancing the endoprosthesis over a first guidewire.

12. The method of claim 11, wherein the side branch component is positioned by advancing the endoprosthesis over a second guidewire.

13. A delivery system for an implantable device, the delivery system comprising:
a delivery device having a shaft;
an expandable implant releasably mounted onto the shaft, the expandable implant constrained toward a radially collapsed configuration by a primary sleeve;
a secondary sleeve overlapping with the primary sleeve, wherein upon release of the primary sleeve, the secondary sleeve releasably constrains at least a portion of the expandable implant to a partially expanded configuration; and
a side branch component configured to be deployed via the portion of the expandable implant in the partially expanded configuration.

14. The delivery system of claim 13, wherein the expandable implant is self-expandable.

15. The delivery system of claim 13, wherein the primary sleeve is formed of a single sheet of material, the primary sleeve defining a plurality of openings configured to receive a single coupling member to secure edges of the single sheet of material to form the primary sleeve.

16. The delivery system of claim 13, wherein the secondary sleeve is formed of a single sheet of material, the secondary sleeve defining a plurality of openings configured to receive a single coupling member to secure edges of the single sheet of material to farm the secondary sleeve.

17. The delivery system of claim 13, wherein release of the primary sleeve and the secondary sleeve results in full expansion of the expandable implant.

18. The delivery system of claim 17, wherein the primary sleeve and the secondary sleeve remain coupled to the expandable implant upon release of the primary sleeve and the secondary sleeve.

19. The delivery system of claim 17, wherein the primary sleeve and the secondary sleeve are rendered removable from the expandable implant upon release of the primary sleeve and the secondary sleeve.

20. The delivery system of claim 13, further comprising a second primary sleeve constraining a portion of the expandable implant otherwise uncovered by the primary sleeve, wherein the second primary sleeve and the secondary sleeve are coupled to the expandable implant in a parallel manner.

21. A delivery system for delivering an implantable device into vasculature of a patient, the delivery system comprising:
a delivery device having a shaft;
an expandable implant including a primary sleeve and a secondary sleeve, the expandable implant releasably mounted onto the shaft and constrained toward a radially collapsed configuration by the primary sleeve, the secondary sleeve overlapping with the primary sleeve such that upon release of the primary sleeve the secondary sleeve releasably constrains a portion of the expandable implant at a partially expanded configuration that defines a deployment space exterior to the expandable implant between the expandable implant and the vasculature of the patient, the deployment space being accessible from within the expandable implant; and
a side branch component configured to be extended from within the expandable implant into the deployment space during deployment of the side branch component.

* * * * *